(12) United States Patent
Albert et al.

(10) Patent No.: US 8,016,886 B2
(45) Date of Patent: Sep. 13, 2011

(54) INTERVERTEBRAL DISC REPLACEMENT DEVICE

(75) Inventors: Todd James Albert, Narberth, PA (US); Richard H. Rothman, Philadelphia, PA (US); Leon Roitburg, East Hanover, NJ (US); Rafail Zubok, Midland Park, NJ (US); Mikhail Kvitnitsky, Clifton, NJ (US)

(73) Assignee: Altus Partners, LLC, Newtown Spuare, PA (US)

( * ) Notice: Subject to any disclaimer, the term of this patent is extended or adjusted under 35 U.S.C. 154(b) by 170 days.

(21) Appl. No.: 11/488,817

(22) Filed: Jul. 18, 2006

(65) Prior Publication Data

US 2008/0065211 A1    Mar. 13, 2008

(51) Int. Cl.
*A61F 2/44*    (2006.01)
(52) U.S. Cl. .................................................... 623/17.11
(58) Field of Classification Search .................... 606/61; 623/17.11–17.16
See application file for complete search history.

(56) References Cited

U.S. PATENT DOCUMENTS

| | | | |
|---|---|---|---|
| 2,499,030 A | 2/1950 | Moon | |
| 3,068,032 A | 12/1962 | Friedrich | |
| 3,441,299 A | 4/1969 | Pfaar | |
| 4,836,485 A | 6/1989 | Cooper | |
| 5,056,951 A | 10/1991 | Mariani | |
| 5,090,654 A | 2/1992 | Ridings et al. | |
| 5,246,458 A | 9/1993 | Graham | |
| 5,480,442 A | 1/1996 | Bertagnoli | |
| 5,562,737 A | 10/1996 | Graf | |
| 5,562,738 A * | 10/1996 | Boyd et al. ................. | 623/17.15 |
| 5,683,465 A | 11/1997 | Shinn et al. | |
| 5,989,291 A | 11/1999 | Ralph et al. | |
| 6,019,792 A | 2/2000 | Cauthen | |
| 6,039,763 A * | 3/2000 | Shelokov ................... | 623/17.16 |
| 6,063,121 A | 5/2000 | Xavier et al. | |
| 6,179,874 B1 | 1/2001 | Cauthen | |
| 6,228,118 B1 | 5/2001 | Gordon | |
| 6,368,350 B1 | 4/2002 | Erickson et al. | |
| 6,440,168 B1 | 8/2002 | Cauthen | |
| 6,478,822 B1 | 11/2002 | Leroux et al. | |
| 6,517,580 B1 * | 2/2003 | Ramadan et al. .......... | 623/17.15 |
| 6,520,996 B1 | 2/2003 | Manasas et al. | |
| 6,540,785 B1 | 4/2003 | Gill et al. | |
| 6,610,092 B2 | 8/2003 | Ralph et al. | |
| 6,616,668 B2 | 9/2003 | Altarac et al. | |
| 6,645,248 B2 | 11/2003 | Casutt | |
| 6,645,249 B2 | 11/2003 | Ralph et al. | |

(Continued)

OTHER PUBLICATIONS

United States Patent and Trademark Office Action for U.S. Appl. No. 11/376,977 dated Dec. 11, 2007.

(Continued)

*Primary Examiner* — Eduardo C Robert
*Assistant Examiner* — Mary Hoffman
(74) *Attorney, Agent, or Firm* — Matthew B. Dernier, Esq.; Gibson & Dernier LLP

(57) ABSTRACT

An intervertebral stabilizer includes: a first member operable to engage an endplate of a vertebral bone of a spine, the first member having top and bottom surfaces defining a thickness therebetween; a second member spaced apart from the first member and operable to engage an endplate of an adjacent vertebral bone of the spine; a connecting element located substantially between and connecting the first and second members; and the first member having at least one slot extending through a portion thereof through its entire thickness and top and bottom surfaces, creating first and second portions of the first member, wherein the slot imparts compressibility and/or expandability to the intervertebral disc replacement device.

37 Claims, 9 Drawing Sheets

U.S. PATENT DOCUMENTS

| | | | |
|---|---|---|---|
| 6,669,730 B2 | 12/2003 | Ralph et al. | |
| 6,669,731 B2 | 12/2003 | Ralph et al. | |
| 6,673,113 B2 | 1/2004 | Ralph et al. | |
| 6,679,915 B1 | 1/2004 | Cauthen | |
| 6,682,562 B2 | 1/2004 | Viart et al. | |
| 6,733,532 B1 | 5/2004 | Gauchet et al. | |
| 6,740,117 B2 | 5/2004 | Ralph et al. | |
| 6,740,118 B2 | 5/2004 | Eisermann et al. | |
| 6,764,515 B2 | 7/2004 | Ralph et al. | |
| 6,770,095 B2 | 8/2004 | Grinberg et al. | |
| 6,802,867 B2 | 10/2004 | Manasas et al. | |
| 6,808,538 B2 | 10/2004 | Paponneau | |
| 6,863,688 B2 | 3/2005 | Ralph et al. | |
| 6,869,446 B2 | 3/2005 | Ralph et al. | |
| 6,994,727 B2 * | 2/2006 | Khandkar et al. | 623/17.15 |
| 7,153,325 B2 * | 12/2006 | Kim et al. | 623/17.15 |
| 7,316,714 B2 | 1/2008 | Gordon et al. | |
| 2002/0111687 A1 | 8/2002 | Ralph et al. | |
| 2003/0014116 A1 | 1/2003 | Ralph et al. | |
| 2003/0040802 A1 * | 2/2003 | Errico et al. | 623/17.14 |
| 2003/0065395 A1 | 4/2003 | Ralph et al. | |
| 2003/0069642 A1 | 4/2003 | Ralph et al. | |
| 2003/0069643 A1 | 4/2003 | Ralph et al. | |
| 2003/0074066 A1 | 4/2003 | Errico et al. | |
| 2003/0074067 A1 | 4/2003 | Errico et al. | |
| 2003/0074068 A1 | 4/2003 | Errico et al. | |
| 2003/0074069 A1 | 4/2003 | Errico et al. | |
| 2003/0074070 A1 | 4/2003 | Errico et al. | |
| 2003/0074071 A1 | 4/2003 | Errico et al. | |
| 2003/0074072 A1 | 4/2003 | Errico et al. | |
| 2003/0074073 A1 | 4/2003 | Errico et al. | |
| 2003/0074074 A1 | 4/2003 | Errico et al. | |
| 2003/0078662 A1 | 4/2003 | Ralph et al. | |
| 2003/0216810 A1 | 11/2003 | Ralph et al. | |
| 2004/0034422 A1 | 2/2004 | Errico et al. | |
| 2004/0034424 A1 | 2/2004 | Errico et al. | |
| 2004/0034425 A1 | 2/2004 | Errico et al. | |
| 2004/0034426 A1 | 2/2004 | Errico et al. | |
| 2004/0122517 A1 * | 6/2004 | Kuras | 623/17.11 |
| 2004/0225295 A1 | 11/2004 | Zubok et al. | |
| 2004/0225365 A1 | 11/2004 | Eisermann et al. | |
| 2004/0254644 A1 * | 12/2004 | Taylor | 623/17.13 |
| 2005/0027363 A1 | 2/2005 | Gordon | |
| 2005/0027364 A1 * | 2/2005 | Kim et al. | 623/17.13 |
| 2005/0055029 A1 | 3/2005 | Marik et al. | |
| 2005/0197703 A1 | 9/2005 | Diaz et al. | |
| 2005/0197704 A1 | 9/2005 | Diaz et al. | |
| 2006/0178746 A1 * | 8/2006 | Bartish et al. | 623/17.13 |
| 2006/0217809 A1 | 9/2006 | Albert et al. | |
| 2007/0073406 A1 | 3/2007 | Gordon et al. | |
| 2007/0100456 A1 * | 5/2007 | Dooris et al. | 623/17.14 |
| 2007/0150062 A1 | 6/2007 | Zubok et al. | |
| 2007/0233255 A1 | 10/2007 | Song et al. | |
| 2008/0065211 A1 | 3/2008 | Albert et al. | |

OTHER PUBLICATIONS

Office Action for co-pending patent U.S. Appl. No. 11/376,977 dated Sep. 21, 1997.

Office Action for co-pending patent U.S. Appl. No. 11/376,977 dated Nov. 9, 2007.

Office Action for co-pending patent U.S. Appl. No. 11/376,977 dated Dec. 15, 2009.

Office Action for co-pending patent U.S. Appl. No. 11/376,977 dated Jun. 23, 2008.

Advisory Action for co-pending patent U.S. Appl. No. 11/376,977 dated Sep. 19, 2008.

Office Action for co-pending patent U.S. Appl. No. 11/376,977 dated Dec. 23, 2008.

Office Action for co-pending patent U.S. Appl. No. 11/376,977 dated Jun. 5, 2009.

International Preliminary Report on Patentability for corresponding PCT application PCT/US2006/009663, Mar. 24, 2009.

* cited by examiner

100

104

104

104

INTERVERTEBRAL DISC REPLACEMENT DEVICE

BACKGROUND

The present disclosure generally relates to apparatus and methods for treatment of spinal disorders using an intervertebral prosthesis which is disposed in an intervertebral disc space following removal of a damaged or diseased intervertebral disc.

The bones and connective tissue of an adult human spinal column consists of more than twenty discrete bones coupled sequentially to one another by a tri-joint complex. Each tri-joint complex includes an anterior disc and two posterior facet joints. The anterior discs of adjacent bones are cushioned by cartilage spacers referred to as intervertebral discs. These more than twenty bones are anatomically categorized as being members of one of four classifications: cervical, thoracic, lumbar, or sacral. The cervical portion of the spine, which comprises the top of the spine, up to the base of the skull, includes the first seven vertebrae. The intermediate twelve bones are the thoracic vertebrae, and connect to the lower spine comprising the five lumbar vertebrae. The base of the spine includes the sacral bones (including the coccyx). The component bones of the cervical spine are generally smaller than those of the thoracic spine, which are in turn smaller than those of the lumbar region. The sacral region connects laterally to the pelvis.

The spinal column is highly complex in that it includes these more than twenty bones coupled to one another, housing and protecting critical elements of the nervous system having innumerable peripheral nerves and circulatory bodies in close proximity. In spite of these complications, the spine is a highly flexible structure, capable of a high degree of curvature and twist in nearly every direction.

Genetic or developmental irregularities, trauma, chronic stress, tumors, and degenerative wear are a few of the causes that can result in spinal pathologies for which surgical intervention may be necessary. A variety of systems have been disclosed in the art that achieve immobilization and/or fusion of adjacent bones by implanting artificial assemblies in or on the spinal column. The region of the back that needs to be immobilized, as well as the individual variations in anatomy, determine the appropriate surgical protocol and implantation assembly. With respect to the failure of the intervertebral disc, the interbody fusion cage has generated substantial interest because it can be implanted laparoscopically into the anterior of the spine, thus reducing operating room time, patient recovery time, and scarification.

Conventional intervertebral body cages generally comprise a tubular metal body having an external surface threading. They are inserted transverse to the axis of the spine, into preformed cylindrical holes at the junction of adjacent vertebral bodies. Two cages are generally inserted side by side with the external threading tapping into the lower surface of the vertebral bone above, and the upper surface of the vertebral bone below. The cages include holes through which the adjacent bones are to grow. Additional materials, for example autogenous bone graft materials, may be inserted into the hollow interior of the cage to incite or accelerate the growth of the bone into the cage. End caps are often utilized to hold the bone graft material within the cage.

The cages of the prior art have enjoyed medical success in promoting fusion and grossly approximating proper disc height. It is, however, important to note that the fusion of the adjacent bones is an incomplete solution to the underlying pathology as it does not cure the ailment, but rather simply masks the pathology under a stabilizing bridge of bone. This bone fusion limits the overall flexibility of the spinal column and artificially constrains the normal motion of the patient. This constraint can cause collateral injury to the patient's spine as additional stresses of motion, normally borne by the now-fused joint, are transferred onto the nearby facet joints and intervertebral discs. It would therefore, be a considerable advance in the art to provide an implant assembly which does not promote fusion, but, rather, which mimics the biomechanical action of the natural disc cartilage, thereby permitting continued normal motion and stress distribution.

An objective in intervertebral disc replacement or intervertebral stabilization is to provide a prosthetic disc that combines both stability to support the high loads of the patient's vertebrae and flexibility to provide the patient with sufficient mobility and proper spinal column load distribution.

Numerous artificial intervertebral discs for replacing a part or all of a removed disc have been developed, namely, elastomer discs, ball and socket discs, mechanical spring discs and hybrid discs. Elastomer discs typically include an elastomer cushion which is sandwiched between lower and upper rigid endplates. The elastomer discs are advantageous in that the elastomer cushion functions similar in mechanical behavior to the removed intervertebral disc tissue. However, a disadvantage of this disc type is that the elastomer cushion experiences long term in-vivo problems stemming from microcracking, which detracts from its usefulness as a replacement option. Furthermore, attachment of the flexible elastomer cushion to rigid endplates presents additional difficulties. Examples of elastomer discs are disclosed in U.S. Pat. Nos. 5,702,450; 5,035,716; 4,874,389; and 4,863,477.

Mechanical spring discs usually incorporate one or more coiled springs disposed between metal endplates. The coiled springs may define a cumulative spring constant sufficient to maintain the spaced arrangement of the adjacent vertebrae and to allow normal movement of the vertebrae during flexion and extension of the spring in any direction. Examples of mechanical spring discs are disclosed in U.S. Pat. Nos. 5,458,642; and 4,309,777.

Ball and socket discs typically incorporate two plate members having cooperating inner ball and socket portions which permit articulating motion of the members during movement of the spine. The ball and socket arrangement is adept in restoring motion of the spine. Examples of ball and socket discs are disclosed in U.S. Pat. Nos. 5,507,816; and 5,258,031. These conventional ball and socket discs include some disadvantageous properties, such as the plate members not remaining interconnected (via the ball and socket) when tensile forces are applied. In other words, the ball is not captured within the socket. While there are existing captured ball and socket discs in the art, they are very complex in the manner in which the ball and socket are interconnected. An example of such a ball and socket configuration is disclosed in U.S. Patent Publication No.: 2003/0069643, the entire disclosure of which is hereby incorporated by reference.

Hybrid artificial intervertebral discs usually incorporate two or more disc types. For example, one known hybrid disc arrangement includes a ball and socket set surrounded by an elastomer ring. This hybrid disc provides several advantages with respect to load carrying ability, but, long term in vivo difficulties with the elastomer cushion remain a concern.

All of the above intervertebral devices suffer from one or more problems, such as being overly complex, difficult to assemble and implant, excessively limit the range of motion of the spine, and/or do not remain assembled in the presence of tensile forces. Thus, there are needs for a new intervertebral stabilizer.

SUMMARY OF THE INVENTION

In accordance with one or more embodiments of the present invention, an intervertebral disc replacement device, includes: a first member operable to engage an endplate of a vertebral bone of a spine, the first member having top and bottom surfaces along various portions thereof, the top and bottom surfaces defining a thickness therebetween; a second member spaced apart from the first member and operable to engage an endplate of an adjacent vertebral bone of the spine; a connecting element located substantially between and connecting the first and second members; and the first member having at least one slot extending through at least one of the various portions thereof through the thickness and top and bottom surfaces, creating first and second portions of the first member, wherein the at least one slot imparts compressibility and/or expandability to the intervertebral disc replacement device. The slot imparts compressibility and/or expandability to the intervertebral disc replacement device through substantially divergent displacement of the first and second portions of the first member at the slot. In addition, in a preferred embodiment, the connecting element is connected to the second portion of the first member while the first member is engaged with the endplate of the vertebral bone of the spine along the top surface of the first portion thereof.

In alternate embodiments, the slot can be multiple slots, and these multiple slots can be linear, curvilinear, a combination thereof, substantially parallel to each other, angular to each other, or any other relation allowing for divergent moveability of the first and second portions of the first member during compression and/or expansion of the spine.

Other aspects, features, advantages, etc. will become apparent to one skilled in the art when the description of the preferred embodiments of the invention herein is taken in conjunction with the accompanying drawings.

BRIEF DESCRIPTION OF THE DRAWINGS

For the purposes of illustrating the various aspects of the invention, there are shown in the drawings forms that are presently preferred, it being understood, however, that the invention is not limited to the precise arrangements and instrumentalities shown.

DETAILS OF THE EMBODIMENTS OF THE INVENTION

Figure 1:
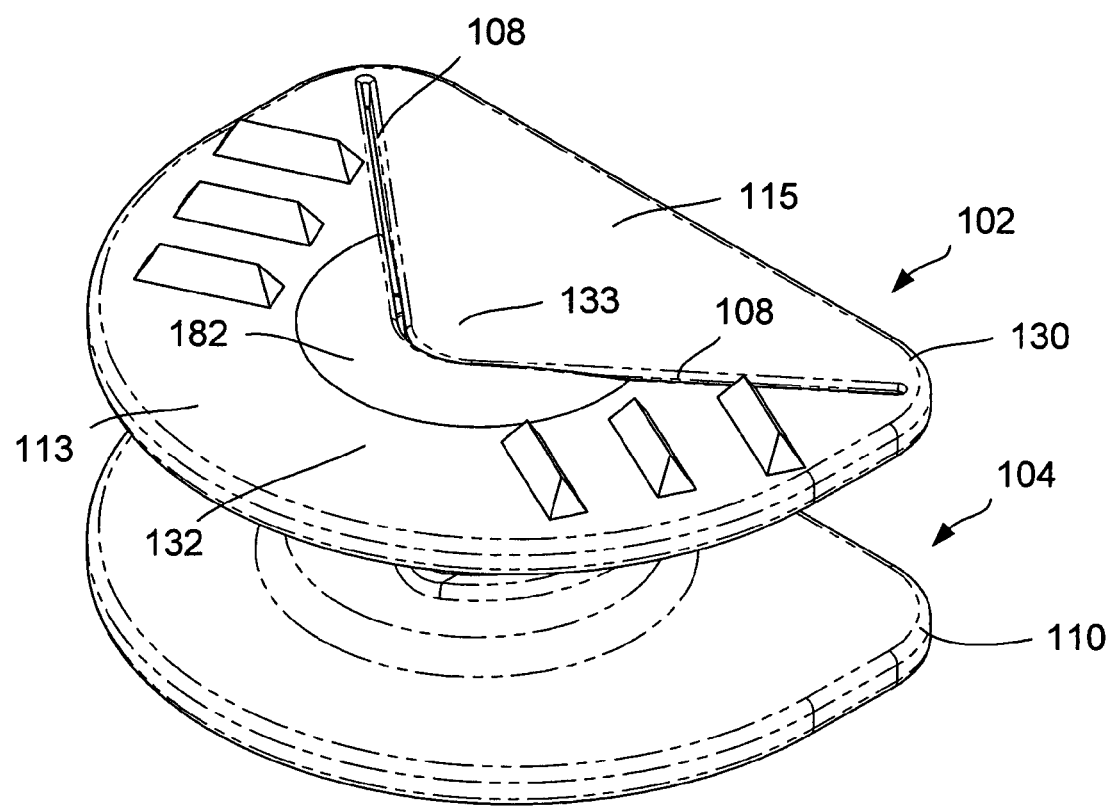
FIG. 1 is a perspective view of an intervertebral disc replacement device in accordance with one or more embodiments of the present invention.
Figure 2:
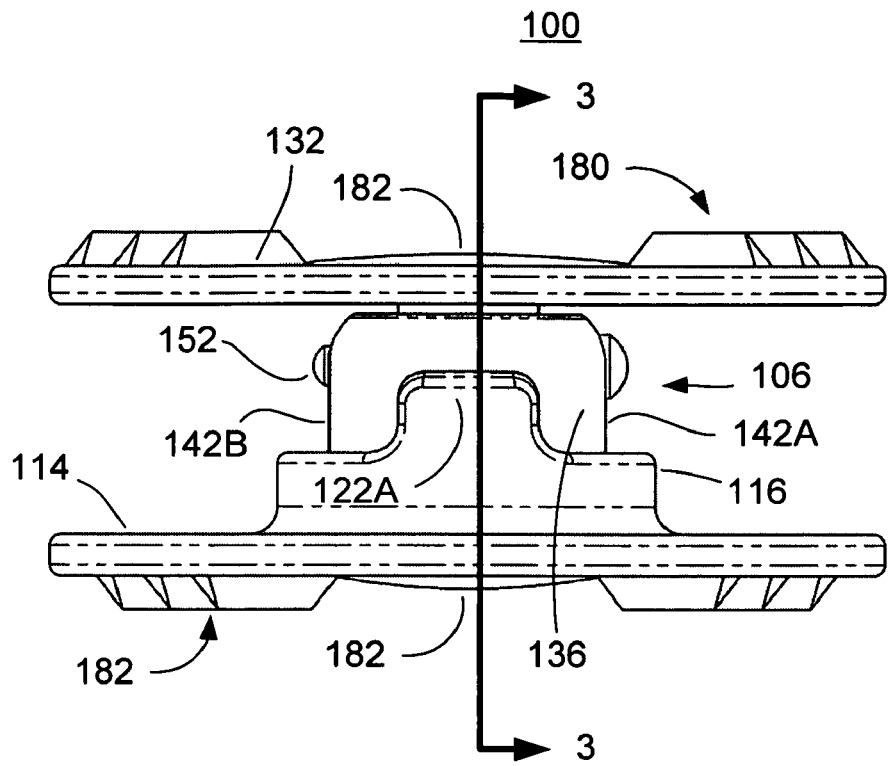
FIG. 2 is a front (anterior) elevational view of the intervertebral disc replacement device of FIG. 1.
Figure 3:
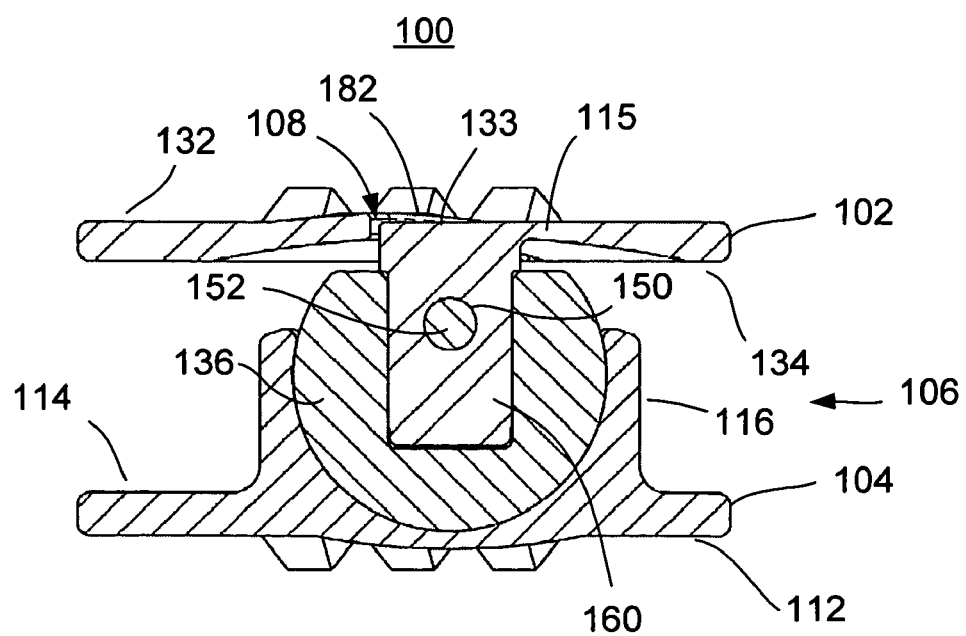
FIG. 3 is a cross-sectional view taken along line 3-3 of the intervertebral disc replacement device of FIG. 2.
Figure 13:
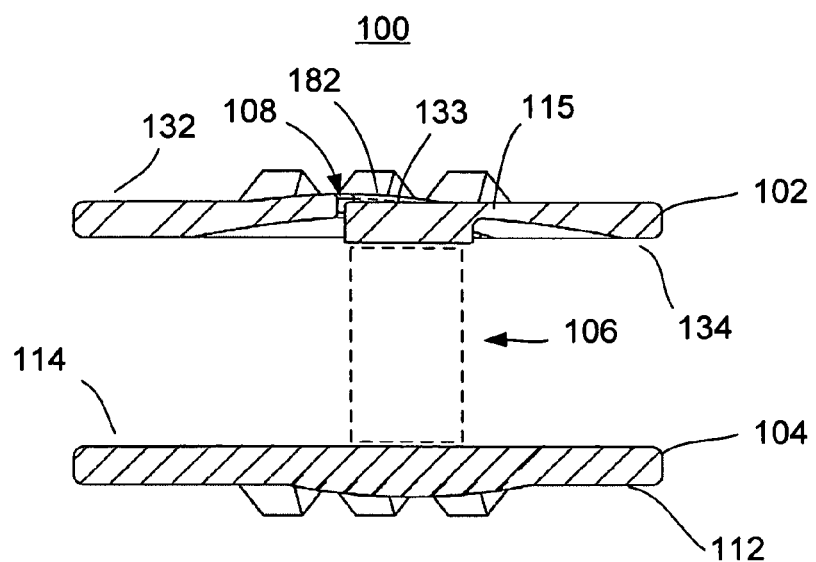
FIG. 13 is a perspective view of an intervertebral disc replacement device in accordance with another embodiment of the present invention.

Reference is now made to FIGS. 1-3, which illustrate an intervertebral disc replacement device 100 in accordance with one or more embodiments of the present invention. FIG. 1 illustrates a perspective view of the intervertebral disc replacement device 100, while FIG. 2 is a front (anterior) view of the device 100. FIG. 3 is a cross-sectional view of the intervertebral disc replacement device 100 taken through line 3-3 (as shown in FIG. 2). The device 100 generally includes two members 102, 104 that are coupled together by way of a ball and socket assembly 106. It is to be understood that reference herein to ball and socket assembly 106 is merely for illustrative purposes only and is not meant to be interpreted in a limiting sense. The present invention anticipates use of any known connecting element 106, such as but not limited to, an elastomer cushion, one or more coiled springs, a combination ball and socket mechanism and an elastomer ring, or any other mechanism or construction known in the art. FIG. 13 shows connecting element 106 as a plain block, illustrative of the fact that any known connecting element is applicable to this invention and covered hereby.

Members 102, 104 are preferably plate members that are preferably, substantially solid throughout their entire thicknesses; apart, however, from the various slot(s) 108, discussed below. This said, however, other embodiments of FIGS. 16 and 17, discussed below, do not have a substantially solid thickness.

The intervertebral disc replacement device 100 is sized and shaped to fit in the intervertebral space between adjacent vertebral bones of the spine. It is understood that the size and shape of the intervertebral disc replacement device 100 may be adapted to fit in an intervertebral space at any level of the spine, such as the cervical spine, thoracic spine, or lumbar spine. The intervertebral disc replacement device 100 is sized and shaped to be inserted into the intervertebral space from an anterior direction.

The member 104 includes a plate 110 of substantially planar configuration, which includes an engagement surface 112 spaced apart from an opposing surface 114. The engagement surface 112 is preferably operable to couple with an end plate of a vertebrae from which an associated disc has been removed. The member 102 preferably includes a plate 130 of substantially planar configuration having an engagement surface 132 and a spaced apart opposing surface 134; such spaced apart distance defining a thickness of member 102. Preferably, the peripheral shape of the plates 110 and 130 are of a complimentary nature with respect to the shape of the corresponding end-plates of the vertebrae. While the engagement surfaces 112, 132 may be substantially flat, such may alternatively include one or more bone adhesion facilitating elements 180, which are operable to promote bone adhesion to the vertebral bones. For example, the bone adhesion facilitating elements 180 may include one or more of spikes, one or more keels, one or more roughening elements, and the like, including but not limited to, holes or grooves in members 102 and/or 104 that are known in the art and can be catalyzed to allow the vertebral bone to grow into and around members 102, 104. In addition, numerous other modifications may be employed on the plates 110, 130, such as angulation elements in any or numerous directions, screws, flanges, coatings, dimples, beads, shock absorption members, etc. One or more of the engagement surfaces 112, 132 may also include a domed portion 182 that is sized and shaped to correspond to the concave shape of the endplates of the vertebral bones.

Continuing with FIGS. 1 and 3, slot(s) 108 are seen to extend entirely through member 102; entirely through the thickness defined between surfaces 132 and 134. In the particular embodiment of FIGS. 1-3, slot(s) 108 are seen to be either one continuous, curvilinear slot, or alternatively, two substantially straight slots connected together at respective ends thereof to form an angular overall slot. Whichever construction is considered applicable, slot(s) 108 of the embodiment of FIGS. 1-3 divides first member 102 into first and second portions 113 and 115, respectively. As is best seen in FIG. 3, second portion 115 is cantilevered and is directly connected to a portion of connecting element 106 of the overall device 100. In contrast, the embodiment of FIGS. 1-3 also shows that elements 180 extend from top surface 132 of first portion 113 of first member 102.

In practice, the nature of the cantilevered construction of portion 115 allows device 100 to have transverse compressibility and/or expandability in essentially upward and downward directions; i.e., upward, or toward the vertebrae to which member 102 is adjacent and/or downward, or toward the vertebrae to which member 104 is adjacent. In particular, and assuming a spine having device 100 installed therein is under compressive forces at least along the portion thereof where device 100 is located, then in this instance, first portion 113 of member 102 and second member 104 will be pushed toward each other. Since slot(s) 108 separate portions 113 and 115, and further since connecting element 106 is connected to second portion 115 of first member 102 (and not to first portion 113), portions 113 and 115 move in substantially divergent directions to each other, thereby allowing device 100 to compress. When device 100 returns from the compressed position, portions 113 and 115 may move in convergent directions towards each other.

Similarly, but this time assuming a spine having device 100 installed therein is being subject to expansive forces at least along the portion thereof where device 100 is located, then in this instance, first portion 113 of member 102 and second member 104 are being pulled apart. Again, since slot(s) 108 separate portions 113 and 115, and further since connecting element 106 is connected to second portion 115 of first member 102 (and not to first portion 113), portions 113 and 115 again move in substantially divergent directions to each other, thereby allowing device 100 to expand. When device 100 returns from the expanded position, portions 113 and 115 may move in convergent directions towards each other.

In both of the above instances it is preferable that top surface 132 have domed portion 182 (discussed above). As best seen in FIG. 3, domed portion 182 provides a gap between a top surface 133 of second portion 115 and top surface 132 at domed portion 182; i.e., top surface 133 of second portion 115 is recessed relative to top surface 132 of domed portion 182, at least at slot(s) 108. The existence of this gap allows for more play to exist between surface 133 and the surface of the vertebrae of the spine thereby giving device 100 more room to compress or expand.

Figure 14:
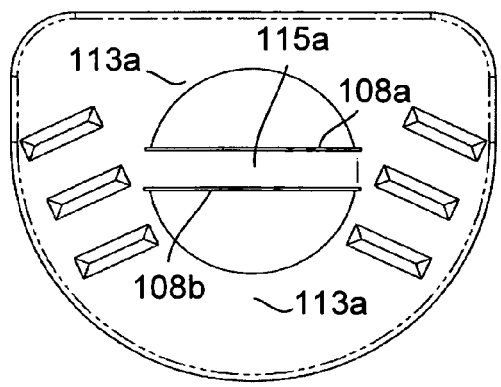
FIG. 14 is a top plan view of another embodiment of a first member of an intervertebral disc replacement device.
Figure 15:
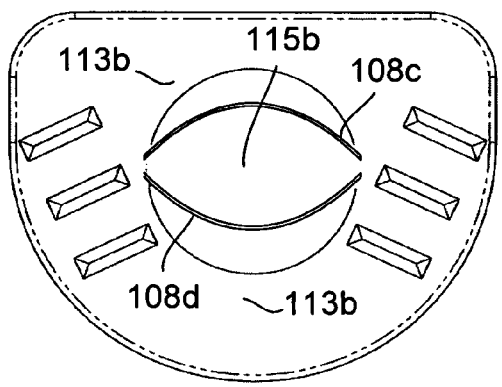
FIG. 15 is a top plan view of yet another embodiment of a first member of an intervertebral disc replacement device.

As is best seen in FIGS. 14 and 15, other embodiments of slot(s) 108 are anticipated. In particular, and by way of example only, and not meant to be construed in a limiting sense, in addition to the angled slot(s) 108 of the embodiment of FIGS. 1-3, it is anticipated at FIG. 14 that two substantially parallel slots 108a and 108b create second portion 115a of member 102 that is flexibly moveable in a substantially transverse direction to first portions 113a. Here again, the transverse moveability of portion 115a is in directions essentially upward, toward the vertebrae adjacent member 102 and essentially downward, toward the vertebrae adjacent member 104. When the movement is "upward", device 100 is in compression. When the movement is "downward", device 100 is in expansion. In addition, when the movement of second portion 115a of FIG. 14 is "upward", any perceived movement (if there is any) of first portion 113a is, in comparison, "downward" toward second member 104.

It is further anticipated at FIG. 15 that two non-connecting, curvilinear slots 108c and 108d create still a different second portion 115b of member 102 that is flexibly moveable in a substantially transverse direction to first portions 113b. Here again, the transverse moveability of portion 115b is in directions essentially upward, toward the vertebrae adjacent member 102 and essentially downward, toward the vertebrae adjacent member 104. As with the discussion immediately above regarding FIG. 14, when the movement is "upward", device 100 is in compression. When the movement is "downward", device 100 is in expansion. In addition, when the movement of second portion 115b of FIG. 15 is "upward", any perceived movement (if there is any) of first portion 113b is, in comparison, "downward" toward second member 104.

In both instances of these alternate embodiments, as with respect to second portion 115 of the embodiment discussed above for FIGS. 1-3, second portions 115a and 115b, respectively, are directly connected to a portion of connecting element 106 of the overall device 100. It is this connection, along with existence of slots 108a, b, c, d, that allows first and second portions 113a, b and 115a, b to move in divergent directions from each other, respectively.

Continuing with a description of the illustrative embodiment of FIGS. 1-3, the ball and socket assembly 106 may include a socket element 116 extending from the opposing surface 114 of the plate 110 in a transverse direction, preferably perpendicular thereto. The ball and socket assembly 106 may also include a ball element 136 extending from the opposing surface 134 of the plate 130, preferably in a transverse direction (e.g., perpendicular). The ball and socket assembly 106 is operable such that the ball element 136 may be received into, and removed from, the socket element 116 in one or more first articulation positions of the plate members 102, 104. Once received into the socket element 116, the ball element 136 may not be removed when the plate members 102, 104 are in one or more second articulation positions. In this regard, the phrase "articulation position" is intended to include within its meaning: articulation (such as orientations of the plates that would result from anterior-posterior flexing and lateral bending of the vertebral bones), rotation, translation, and/or any combination of the above motions/orientations of the plate members 102, 104. Also, the word "articulation" is intended to include within its meaning: articulation (such as orientations of the plates that would result from anterior-posterior flexing and lateral bending of the vertebral bones), rotation, translation, and/or any combination of the above motions.

Figure 4:
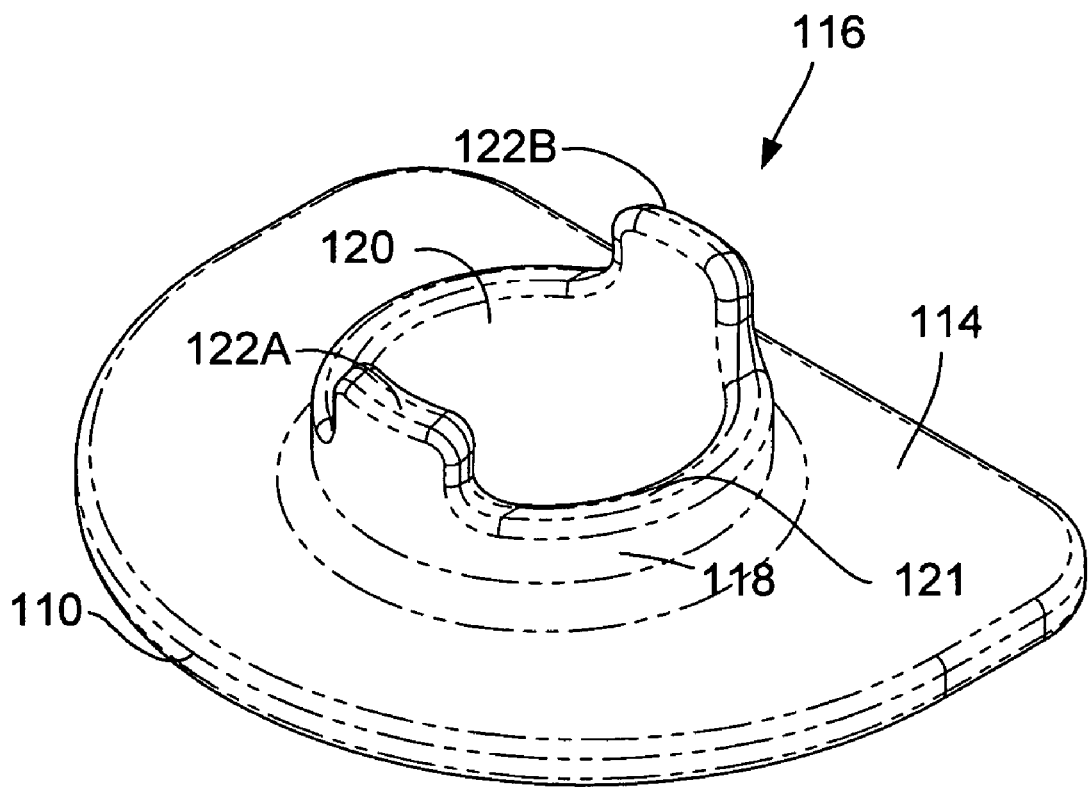
FIG. 4 is a perspective view of a plate member of the intervertebral disc replacement device of FIG. 1.
Figure 5:
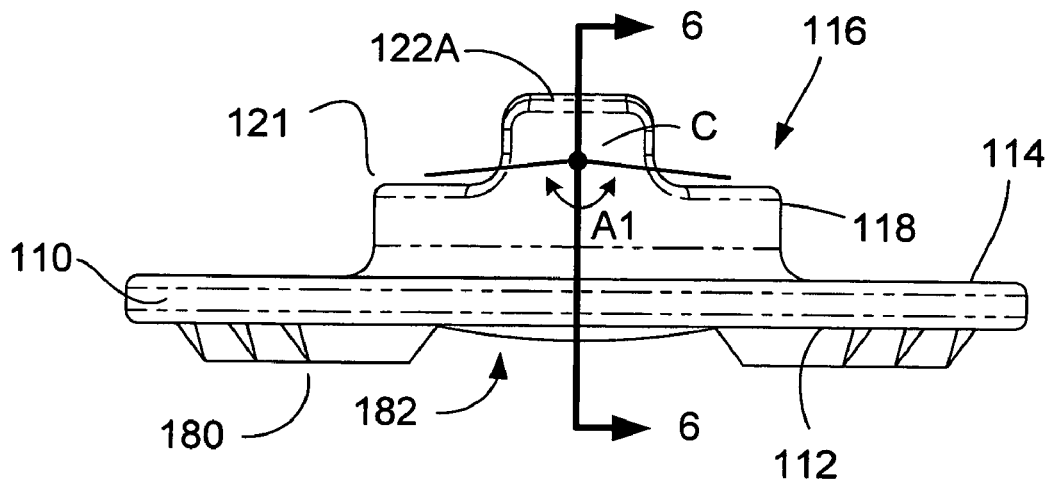
FIG. 5 is a front (anterior) elevational view of the plate member of FIG. 4.
Figure 6:
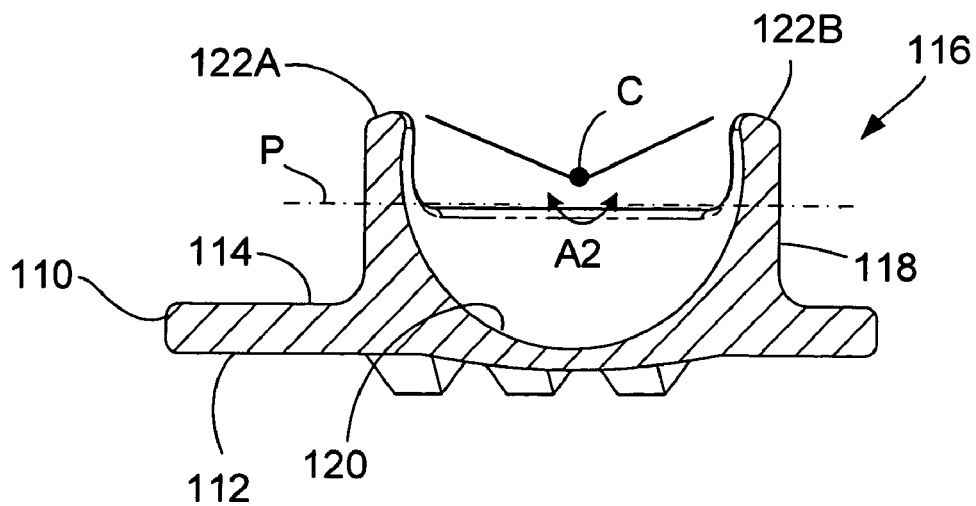
FIG. 6 is a cross-sectional view taken along line 6-6 of the plate member of FIG. 5.

With reference to FIGS. 4-6, further details regarding the plate member 104 will now be provided. FIG. 4 is a perspective view of the plate member 104, while FIG. 5 is a front (anterior) view thereof. FIG. 6 is a cross-sectional view of the plate member 104 taken through line 6-6 (as shown in FIG. 5). The socket element 116 includes an annular wall 118 defining an interior surface 120, wherein the interior surface 120 is of a size and shape to permit articulation of the ball element 136 therein.

Figure 7:
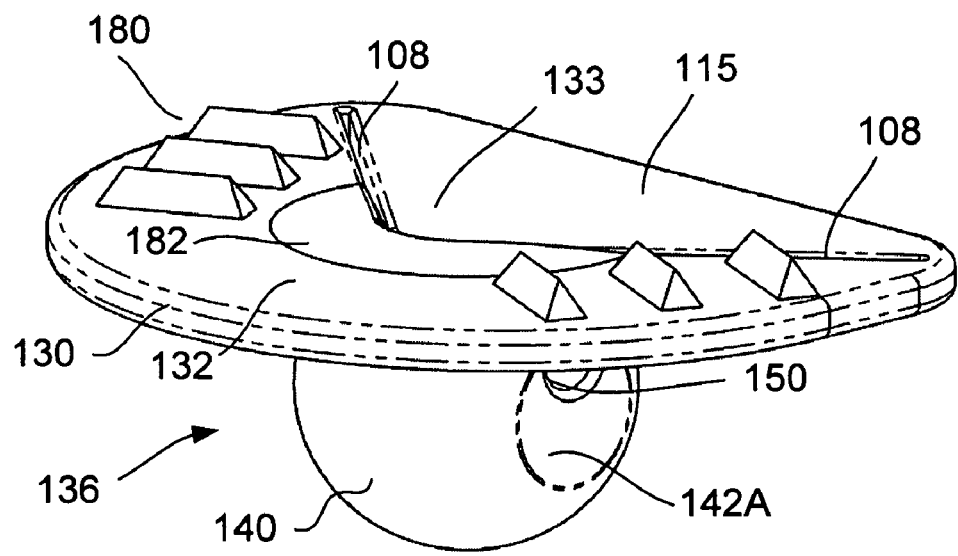
FIG. 7 is a perspective view of another plate member of the intervertebral disc replacement device of FIG. 1.
Figure 8:
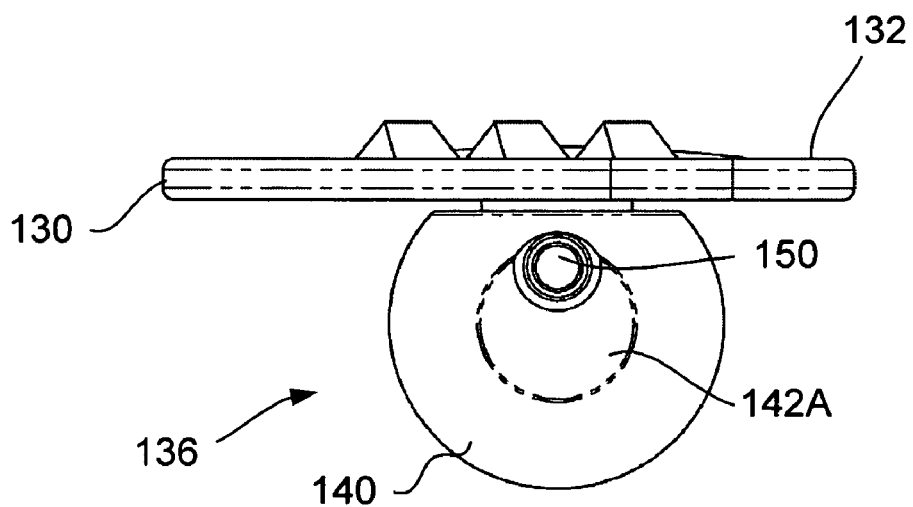
FIG. 8 is a side (lateral) elevational view of the plate member of FIG. 7.
Figure 9:
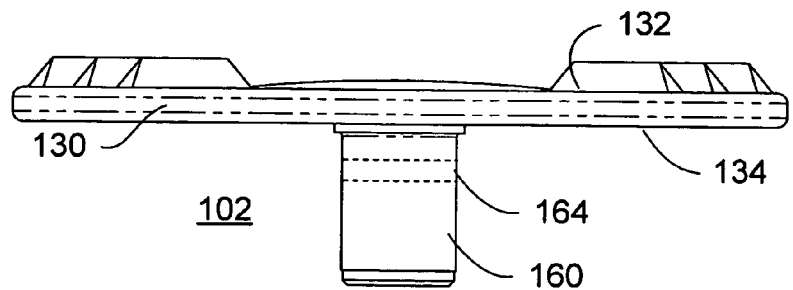
FIG. 9 is a front (anterior) elevational view of an embodiment of the plate member of FIG. 7.

With reference to FIGS. 7-8, which illustrate views of the plate member 102, the ball element 136 includes an outer surface 140 having a first contour. The interior surface 120 of the socket member 116 has a second contour defining a volume. The first and second contours preferably complement one another such that the ball element 116 may articulate within the volume of the socket element 116. For example, the interior surface 120 of the socket element 116 and the outer surface 140 of the ball element 136 may define respective, substantially spherical configurations. It is noted, however, that the interior surface 120 of the socket element 116 need not define a complete sphere, but rather a partial sphere having an edge that terminates along a peripheral edge 121 of the annular wall 118.

At least a portion of the peripheral edge 121 of the inner surface 120 of the socket element 116 may define a profile that, together with the first contour of the ball element 136, achieves the aforementioned assembly and capture functions—that the ball element 136 may be received into, and removed from, the socket element 116 in one or more first articulation positions of the plate members 102, 104, but once received into the socket element 116, the ball element 136 may not be removed when the plate members 102, 104 are in one or more second articulation positions. For example, when the plate member 102 is in the orientation illustrated in FIG. 8 and the plate member 104 is in the orientation illustrated in FIG. 5, the ball element 136 may be received into, and removed from, the socket element 116—they may be assembled. On the other hand, once assembled, as in FIG. 3, the plate members 102, 104 are in different relative orientations and the ball element 136 may not be removed from the socket element 116—the ball element 136 is captured within the socket element 116.

In one or more embodiments, one or both of the ball element 136 and the socket element 116 may include keyed surfaces or keyed portions that operate together to achieve the assembly and/or capture functions. For example, the first contour of the outer surface 140 of the ball element 136 may include one or more keyed surfaces, such as one or more flat portions 142 (two such flat portions 142A, 142B being shown by way of example—although any number may be employed). Additionally, the profile of the peripheral edge 121 of the inner surface 120 of the socket element 116 may include at least one corresponding keyed portion. By way of example, the annular wall 118 may include one or more stand-offs 122 (two such stand-offs 122A, 122B being shown by way of example—although any number may be employed). While some portions of the peripheral edge 121 lay in a plane P (see FIG. 6), the portions of the peripheral edge 121 at the stand-offs 122A, 122B, extend beyond the plane P. The assembly function is permitted only when the keyed surfaces (flat portions) 142A, 142B of the ball element 136 are positioned in sliding relation to the corresponding keyed portions (stand-offs 122A, 122B) of the socket element 116. In particular, this orientation of the plate members 102, 104 permits the flat portions 142A, 142B of the ball member 136 to slide relative to the one or more stand-offs 122A, 122B of the socket element 116 as the ball element 136 is received into, and/or extracted from the socket element 116.

The one or more flat portions 142 interrupt the spherical shape of the ball element 136, reducing a diameter of the ball element 136 in at least one axis. Preferably, the size and position of the one or more flat portions 142 are such that they compliment the positions of the stand-offs 122 of the socket 116 and permit the ball element 136 to slide past the stand-offs 122 and into the socket element 116 when in the correct orientation(s). In the illustrated example, the ball member 136 includes two flat portions 142A, 142B that are disposed substantially opposite to one another and in a configuration that is rotationally offset from the positions of the stand-offs 122A, 122B. In other words, the two flat portions 142A, 142B define an axis (passing therethrough) that is rotationally offset from and axis passing through the stand-offs 122A, 122B. This rotational offset is best seen in FIGS. 1-3, where the axes would be transverse to one another.

Thus, to couple the plate members 102, 104 together, the plate members 102, 104 are preferably rotated (e.g., 90 degrees) with respect to one another (see FIGS. 5 and 8) and the ball element 136 is inserted into the socket element 116 such that the flat portions 142A, 142B pass in an abutted relationship to the stand-offs 122A, 122B. The surface 140 of the ball 136 eventually engages the interior surface 120 of the socket 116. Then, the plate members 102, 104 may be rotated with respect to one another such that the flat portions 142A, 142B are not in abutted relationship with the stand-offs 122A, 122B and the ball element 136 is captured within the socket element 116. Once the ball element 136 is captured within the socket element 116, and implanted in a intervertebral disc space of a patient, the one or more articulation positions that permit assembly/disassembly are at least unlikely to be repeated—and are preferably impossible to repeat.

As best seen in FIGS. 5-6, the assembly and capture of the ball element 136 in the socket element 116 are achieved by way of the differing curvature features provided by the contour of the interior surface 120 and peripheral edge 121 thereof. For example, one or more bisecting-cross sections of the inner surface 120 define arcs (e.g., arc A1 in FIG. 5) of less than or equal to 180 degrees, while one or more other bisecting cross-sections of the inner surface 120 define arcs (e.g. arc A2 in FIG. 6) of greater than 180 degrees. The contour of the interior surface 120 (and the peripheral edge 121 thereof) cannot capture the ball element 136 when the bisecting-cross section(s) of the inner surface 120 defines and arc (or arcs) of less than or equal to 180 degrees. At the stand-offs 122A, 122B, however, the contour of the interior surface 120 (and the peripheral edge 121 thereof) can capture the ball element 136 because the bisecting-cross section(s) of the inner surface 120 there define arcs of greater than 180 degrees. The diameter of the opening (or profile) into the socket element 116 at the stand-offs 122A, 122B is smaller than the maximum diameter of the inner surface 120 generally, and smaller than the diameter across other portions of the peripheral edge 121. Owing to the corresponding smaller diameter of the ball element 136 through the flat portions 142A, 142B, the ball member 136 may clear the peripheral edge 121 of the socket element 116 when the flat portions 142A, 142B are aligned with the stand-offs 122A, 122B. (It is noted that this alignment may happen when an axis normal to the flat surface(s) 142 is substantially parallel to and/or co-planar with a plane defined by one of the bisecting cross-sections of the inner surface 120 of greater than 180 degrees.

Once captured, the ball element 136 and the socket element 116 are sized and shaped such that the plate members 102, 104 may achieve various rotational positions without losing the capture of the ball element 136 within the socket element 116. Indeed, in these rotational positions, the plate members 102, 104 may experience tensile forces without separating because the ball element 136 is captured within the socket element 116. When the amount of rotation of the first and second members 102, 104 is such that the flat portions 142 abut the stand-offs 122, however, the plate members 102, 104 cannot withstand tensile forces and may separate (e.g., the ball element 136 may exit from the socket element 116). Further, the spherical nature of the socket element 116 and the ball element 136 is such that numerous and various articulations may be achieved with respect to the plate members 102, 104. Thus, when the device 100 is inserted between vertebrae (and are attached thereto) the device 100 may aid in the articulation between the vertebrae.

With reference to FIGS. 2, 3, and 8, in one or more alternative embodiments, the ball element 136 may include an aperture 150 extending through at least one flat portion 142, such as from one flat portion 142A to the other flat portion 142B. The aperture 150 may accommodate the insertion of a pin 152 (FIG. 12), which pin 152 may prevent rotation of the plate members 102, 104 with respect to one another beyond a predetermined articulation positions, thereby insuring the ball element 136 remains captured within the socket element 116. In other words, the pin 152 may be operatively connectable to the ball element 136 via the aperture 150 after insertion into the socket element 116 such that the pin 152 is operable to prevent the plate members 102, 104 from obtaining the one or more first articulation positions. At the predetermined articulation positions, the pin 152 engages one or more structures of the socket element 116, such as the stand-offs 122A, 122B. It is noted that the limit in articulation as between the plate members 102, 104 may be a desirable feature, as the articulation between adjacent vertebral bones of a healthy spine is limited by various anatomical structures (such as facets, ligaments, etc.) The degree to which the articulation of the plate members 102, 104 is limited may be adjusted by the placement of the keyed surfaces of the socket element 116 with respect to the pin 152. In the illustrated embodiment (see FIGS. 2-3), the angular positions of the pin 152 with respect to the stand-offs 122A, 122B determines the permissible articulation of the plate members 102, 104.

Figure 10:
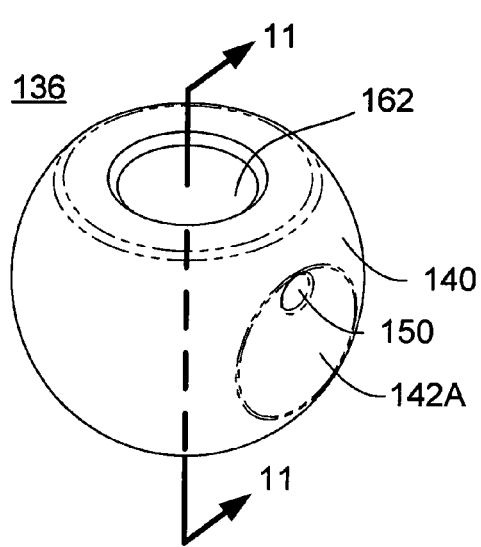
FIG. 10 is a perspective view of a ball member of an embodiment of the plate member of FIG. 7.
Figure 12:
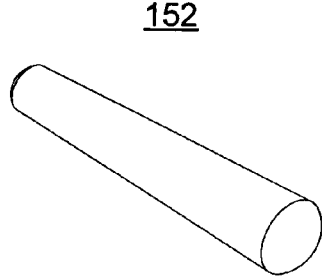
FIG. 12 is a perspective view of a pin for locking together the elements of the intervertebral disc replacement device.
Figure 11:
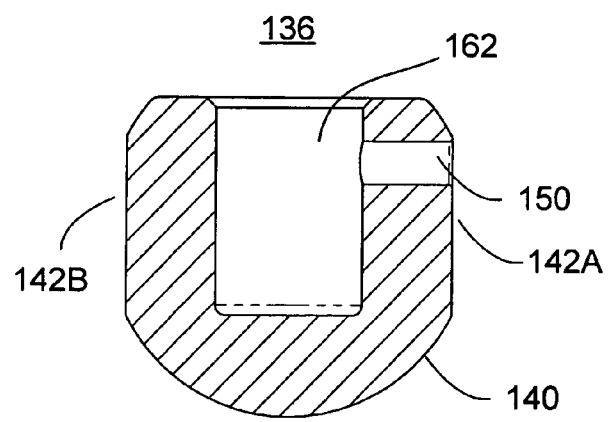
FIG. 11 is a cross-sectional view taken along line 11-11 of the ball member of FIG. 10.

With reference to FIGS. 10-11 (FIG. 11 being a cross-sectional view of FIG. 10 taken through line 11-11), in one or more alternative embodiments, the plate member 102 may include a shaft 160 extending transversely from the opposing surface 134. The ball element 136 may include a bore 162 sized and shaped to receive the shaft 160, thereby coupling the ball element 136 to the plate member 102. The shaft 160 and bore 162 may be fixed to one another via any suitable means, such as adhesives, fusion, shrink fit (temperature, interference fit), etc. Alternatively, the shaft 160 may include a bore 164 that may be placed in registration with the aperture 150 of the ball element 136. The pin 152 may be sized and shaped to engage the respective bores 150, 164 to fix the ball element 136 to the shaft 160. The pin 152 may perform another function, as discussed above, which is to prevent the plate members 102, 104 from obtaining the one or more first articulation positions, thereby capturing the ball element 136 within the socket element 116. As illustrated in FIG. 12, the pin 152 may include at least a conically shaped portion.

Advantageously, the substantially two-piece construction of the device 100 permits a surgeon to select, mix, and match the plate members 102, 104 during surgery. This may accommodate the particular anatomy of the patient such as differing sized vertebrae, etc., which may best be evaluated during surgery. Moreover, once the surgeon has selected the plate members 102, 104, they may be easily coupled together and implanted as one piece.

Figure 16A:
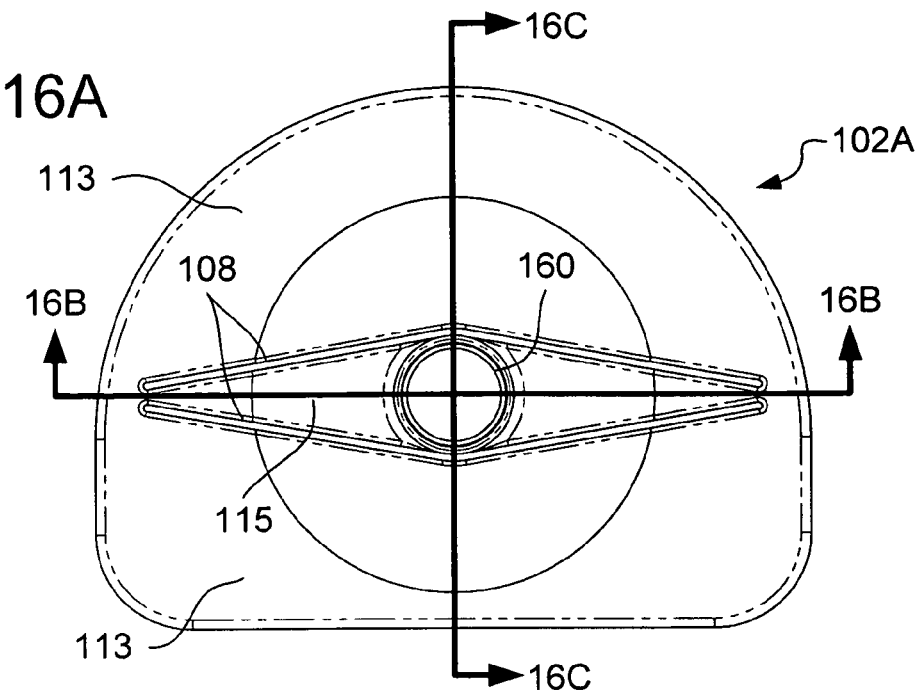
FIGS. 16A, 16B, and 16C are bottom, and two cross-sectional views, respectively, of an intervertebral disc replacement device in accordance with yet another embodiment of the invention.
Figure 16B:
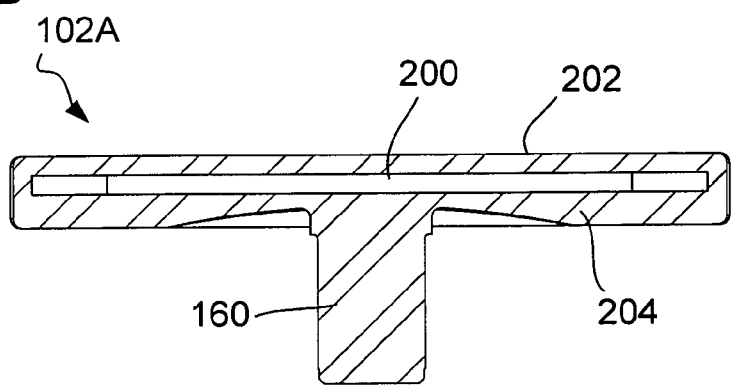
Figure 16C:
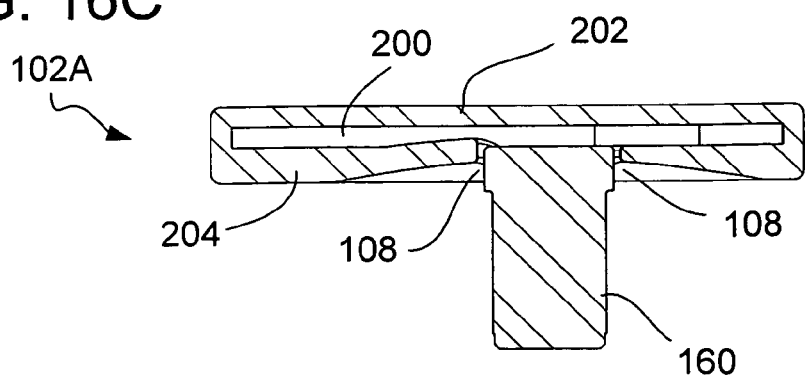

Turning now to a discussion of an alternate embodiment of the invention as shown in FIGS. 16A-C, the intervertebral disc replacement device 100 may employ an alternative first plate member 102A in combination with any known connecting element 106 and any known second member 104. In this embodiment, the first plate member 102A has a construction wherein its thickness is not substantially solid, but instead wherein a cavity 200 or other known type of hollowed out area is found in the plate member 102A. By making the plate member 102A with a cavity 200 formed between an upper member 202 and a lower member 204, it is seen that a deforming of lower member 204 is allowed; i.e., into cavity 200 when member 102A is in compression, and away from cavity 200 when member 102A is in tension/expansion.

While some embodiments of the present invention may have a continuous lower member 204 (with no slot) having extending therefrom the connecting element 106, the illustrated embodiment of FIGS. 16A-C show that slots 108 may be employed in lower member 204 thereby allowing lower member 204 to move as earlier described with respect to upper member 202. In other words, slots 108 define portions 113 and 115, which permit the movement of the lower member 204. In this embodiment, it is anticipated that upper member 202 will be substantially rigid allowing for substantially all of the deformation of member 102A to be at lower member 204. In addition, and if used, bone adhesion facilitating elements 180 may extend from a top surface of upper member 202 of member 102A in order to help promote bone adhesion of device 100 to the vertebral bone above member 102A.

Figure 17A:
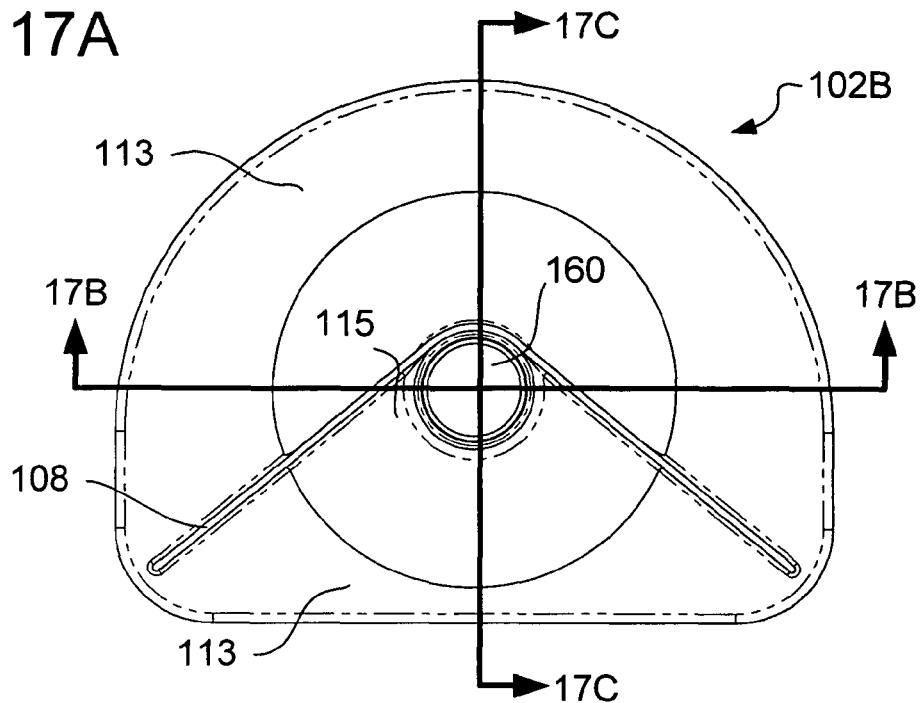
FIGS. 17A, 17B, and 17C are bottom, and two cross-sectional views, respectively, of an intervertebral disc replacement device in accordance with yet another embodiment of the invention.
Figure 17B:
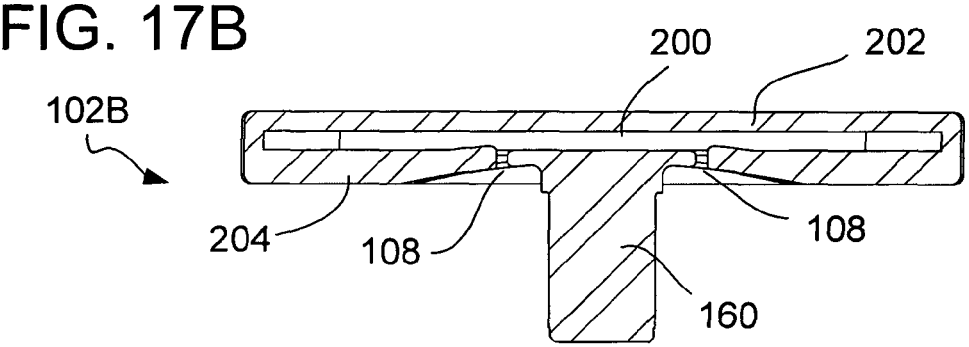
Figure 17C:
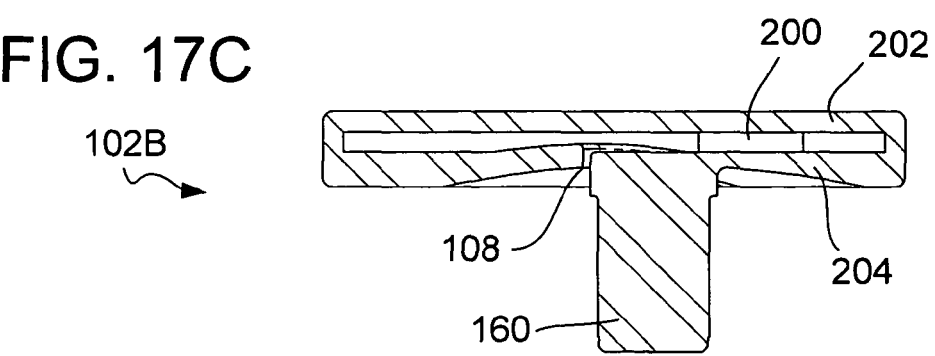

While the embodiment illustrated in FIGS. 16A-C employed two slots 108, an alternative embodiment illustrated in FIGS. 17A-C employs a plate member 102B having one slot 108 in the lower member 204 to define the portions 113, 115 and permit the compression and/or expansion of the plate members 102A, 104 with respect to one another.

It is to be noted that pursuant to the earlier discussions, portion 115 may deform in an expanded (not shown) position, extending away from cavity 200, as opposed to into cavity 200. It is also to be understood that any of the slot arrangements discussed with respect to the earlier embodiments may be used.

Throughout this disclosure the embodiments have shown and discussed member 102 (i.e., the top member of device 100) having slot(s) 108 and/or cavity 200. It is to be understood, however, that no such restrictive interpretation is to be gleaned from this disclosure, and it is instead expressly anticipated herein that either member 102 or member 104 could carry the slot(s) and/or cavity of this invention. It is even further anticipated that both members 102 and 104 can bear the slot(s) and/or cavity of this invention. While this latter construction is less likely, as such a construction might cause device 100 to impart too much flexibility to the person's spine, if appropriately formulated materials were used for members 102 and 104 the flexibility of these members could be controlled within allowable limits. It is not believed that additional figures representing these further alternate embodiments are needed herein to impart the invention to one of ordinary skill in the art, and instead, the constructions of the shown embodiments are applicable to the constructions which would be required were member 104 to be deformable in accordance with the intended of the invention.

As device 100 of this invention is meant to deform as discussed earlier herein, a resilient material is preferably used for its construction. In this regard, it is anticipated that device 100 be made from Titanium, although other resilient and durable materials are also anticipated herein.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. An intervertebral disc replacement device, comprising:
a first member operable to engage an endplate of a vertebral bone of a spine, the first member having top and bottom surfaces along various portions thereof, the top and bottom surfaces defining a thickness therebetween;
a second member spaced apart from the first member and operable to engage an endplate of an adjacent vertebral bone of the spine;
a connecting element located substantially between and connecting the first and second members; and
the first member having at least one slot extending through at least one of the various portions thereof through the thickness and top and bottom surfaces, creating first and second portions of the first member, wherein the at least one slot imparts transverse compressibility and expandability from at least an implanted position to the intervertebral disc replacement device along a direction normal to a plane parallel to the first and second members through substantially divergent displacement of the first and second portions of the first member with respect to one another at the at least one slot in response to movement of respective vertebral bones.

2. The intervertebral disc replacement device of claim 1, wherein the first and second portions of the first member each have top surfaces and further wherein one of the top surfaces of the first and second portions is recessed at least at the at least one slot relative to the other one of the top surfaces of the first and second portions.

3. The intervertebral disc replacement device of claim 2, wherein the top surface of the second portion of the first member is recessed at least at the at least one slot relative to the top surface of the first portion of the first member.

4. The intervertebral disc replacement device of claim 1, wherein the connecting element is connected to the second portion of the first member.

5. The intervertebral disc replacement device of claim 4, wherein the top surface of the first portion of the first member is shaped to be engaged with the endplate of the vertebral bone of the spine.

6. The intervertebral disc replacement device of claim 5, further comprising one or more bone adhesion facilitating elements disposed on at least one of the first and second members, and operable to promote bone adhesion to the vertebral and adjacent vertebral bones.

7. The intervertebral disc replacement device of claim 6, wherein any bone adhesion facilitating elements disposed on the first member, are disposed on the first portion of the first member.

8. The intervertebral disc replacement device of claim 6, wherein the one or more bone adhesion facilitating elements includes at least one of:

one or more spikes extending from at least one of the first and second members for promoting engagement thereof with the associated vertebral bones;
one or more keels extending from at least one of the first and second members for promoting engagement thereof with the associated vertebral bones; and
one or more roughening elements one at least one of the first and second members for promoting engagement thereof with the associated vertebral bones.

9. The intervertebral disc replacement device of claim 4, wherein the at least one slot causes the second portion of the first member to be cantilevered.

10. The intervertebral disc replacement device of claim 1, wherein the at least one slot are two slots.

11. The intervertebral disc replacement device of claim 10, wherein the two slots are connected to each other and form an angle therebetween.

12. The intervertebral disc replacement device of claim 10, wherein the two slots are spaced apart from one another.

13. The intervertebral disc replacement device of claim 12, wherein the spaced apart slots are substantially parallel to each other.

14. The intervertebral disc replacement device of claim 10, wherein either of the two slots can be any shape and length so long as their combination imparts the required compressibility and/or expandability to the intervertebral disc replacement device.

15. The intervertebral disc replacement device of claim 1, wherein the first and second members are plate members.

16. The intervertebral disc replacement device of claim 1, wherein a portion of the connecting element is uniformly formed with either the first member or the second member.

17. The intervertebral disc replacement device of claim 16, wherein another portion of the connecting element, which cooperates with the portion of the connecting element, is uniformly formed with the other of either the first member or the second member.

18. The intervertebral disc replacement device of claim 1, wherein the connecting element is a ball and socket mechanism.

19. The intervertebral disc replacement device of claim 1, wherein the connecting element is an elastomer cushion.

20. The intervertebral disc replacement device of claim 1, wherein the connecting element is one or more coiled springs.

21. The intervertebral disc replacement device of claim 1, wherein the connecting element is a combination ball and socket mechanism and an elastomer ring.

22. The intervertebral disc replacement device of claim 1, the first member further comprising an upper member and a lower member defining a cavity therebetween, wherein the top and bottom surfaces of the first member are top and bottom surfaces of the lower member.

23. The intervertebral disc replacement device of claim 22, wherein compressibility and/or expandability of the intervertebral disc replacement device is achieved through substantially divergent displacement of the first and second portions of the lower member of the first member at the at least one slot.

24. The intervertebral disc replacement device of claim 23, wherein the connecting element is connected to the second portion of the lower member.

25. The intervertebral disc replacement device of claim 24, wherein the upper member of the first member is shaped to be engaged with the endplate of the vertebral bone of the spine along its top surface.

26. The intervertebral disc replacement device of claim 25, further comprising one or more bone adhesion facilitating elements disposed on at least one of the lower member of the first member and the second member, and operable to promote bone adhesion to the vertebral and adjacent vertebral bones.

27. The intervertebral disc replacement device of claim 22, wherein the at least one slot causes the second portion of the lower member to be cantilevered.

28. The intervertebral disc replacement device of claim 22, wherein the at least one slot are two slots.

29. The intervertebral disc replacement device of claim 28, wherein the two slots are connected to each other and form an angle therebetween.

30. The intervertebral disc replacement device of claim 28, wherein the two slots are spaced apart from one another.

31. The intervertebral disc replacement device of claim 30, wherein the spaced apart slots are substantially parallel to each other.

32. The intervertebral disc replacement device of claim 28, wherein either of the two slots can be any shape and length so long as their combination imparts the required compressibility and/or expandability to the intervertebral disc replacement device.

33. The intervertebral disc replacement device of claim 22, wherein the connecting element is a ball and socket mechanism.

34. The intervertebral disc replacement device of claim 22, wherein the connecting element is an elastomer cushion.

35. The intervertebral disc replacement device of claim 22, wherein the connecting element is one or more coiled springs.

36. The intervertebral disc replacement device of claim 22, wherein the connecting element is a combination ball and socket mechanism and an elastomer ring.

37. An intervertebral disc replacement device, comprising:
a first member operable to engage an endplate of a vertebral bone of a spine, the first member having top and bottom surfaces defining a thickness therebetween;
a second member spaced apart from the first member and operable to engage an endplate of an adjacent vertebral bone of the spine;
a connecting element located substantially between and connecting the first and second members; and
the first member having at least one slot extending through a portion thereof through its entire thickness and top and bottom surfaces, creating first and second portions of the first member, wherein the at least one slot imparts vertical compressibility and expandability from at least an implanted position to the intervertebral disc replacement device through substantially divergent displacement of the first and second portions of the first member with respect to one another at the at least one slot in response to movement of respective vertebral bones, and the at least one slot permits the first portion and/or second portion of the first member to converge towards and/or diverge from the second member while the first portion converges towards and/or diverges from the second portion.

* * * * *